United States Patent [19]

Gueyne et al.

[11] Patent Number: 5,609,878

[45] Date of Patent: Mar. 11, 1997

[54] INSECTICIDE COMPOSITION OF ROTENONE MICROSPHERES

[76] Inventors: Jean Gueyne; Marie-Christine Seguin, both of Perigord 1, 6, lacets Saint-Leon, MC-98000 Monte-Carlo, Monaco

[21] Appl. No.: 583,534

[22] Filed: Jan. 5, 1996

Related U.S. Application Data

[63] Continuation of Ser. No. 157,106, filed as PCT/FR92/00490 Jun. 3, 1992 published as WO92/21242 Dec. 10, 1992, abandoned.

[30] Foreign Application Priority Data

Jun. 5, 1991 [JP] Japan .................................. 3-06797

[51] Int. Cl.$^6$ ...................................................... A01N 25/28
[52] U.S. Cl. ........................... 424/408; 424/417; 424/418; 424/490; 514/65; 514/70; 514/73
[58] Field of Search .................................. 424/490, 497, 424/78.31, 78.35, 417, 405, 418, 408; 514/65, 68, 70, 72, 73

[56] References Cited

U.S. PATENT DOCUMENTS

| | | | |
|---|---|---|---|
| 1,945,312 | 1/1934 | Haller et al. . | |
| 1,967,024 | 7/1934 | Fulton et al. | 167/24 |
| 2,194,446 | 3/1940 | Neu et al. . | |
| 3,539,465 | 11/1970 | Hiestand et al. | 252/316 |
| 3,549,555 | 12/1970 | Hiestand et al. . | |
| 4,076,799 | 2/1978 | Willer et al. | 424/45 |
| 4,856,541 | 8/1989 | Kellet et al. | 132/110 |
| 5,275,819 | 1/1994 | Amer et al. | 424/408 |

FOREIGN PATENT DOCUMENTS

| | | |
|---|---|---|
| 0274961 | 7/1988 | European Pat. Off. . |
| 1572106 | 6/1969 | France . |
| 2304326 | 10/1976 | France . |
| 2526632 | 11/1983 | France . |
| 559647 | 2/1946 | United Kingdom . |
| 999960 | 7/1965 | United Kingdom . |

*Primary Examiner*—Neil S. Levy

[57] ABSTRACT

Insecticide composition, especially a pediculicide, comprising as active agent, rotenone or reduced rotenone. The composition is characterized in that said agent is bound to small polymer spherules. The retonone and/or reduced is preferably at least 90% pure. The composition may be in the form of a suspension, an emulsion, a powder, a paste, a cream or a foam and the like. The novel composition is useful in the treatment of parasites in both humans and animals.

20 Claims, No Drawings

INSECTICIDE COMPOSITION OF ROTENONE MICROSPHERES

This is a Continuation of application Ser. No. 08/157, 106, filed as PCT/FR92/00490 on Jun. 3, 1992 published as WO92/21242 on Dec. 10 1992, now abandoned.

The invention relates to a new family of pesticides or insecticides and a means for the destruction of insects, specially parasites in human or animal body; particularly it aims at—humans and animal sarcopticide products and, more particularly destined against sheep scab—pediculicide products and, primarily, compositions for the destruction of lice and their nits. It enables one to fight against a carycites, Dermatophagoides pteronyssins or/and farinae, Hypoderma bovis and tincatum, and against the cochlionyiae hominivorax worm or larvae.

There are a number of products known in this field, for example organochlorinated such as Lindane, D.D.T., organophosphorous, such as Malathion, Parathion and natural or synthetic pyrethrins, associated or not to piperonyl butoxide. All these insecticides are more or less efficient, for the insects acquire habituational resistance. Besides apart from pyrethrin, they leave residue and are not biodegradable. Organochlorinated materials are not destructible and are found in water and in nature; they are stored in animal fat and destroy the nerve layer of myeline. With the organophosphorous, we can notice a phenomenon of selection of resisting clones, requiring the use of more performant and therefore more toxic organophosporous.

In fact, in spite of all these products, we are, at the moment, experiencing real extoparasite invasions in different countries, caused by the fact that the eggs, especially those of pediculides, are very difficult to destroy, and the insects themselves are becoming with time resistant to active substances used. A period of lull, after the death of the major part of the insects, is generally followed by the hatching of a new generation of parasites. It is all the more so since, in addition to the fact that is a risk of a short and long term intoxication of the treated subject, the extended action of the insecticide is not possible. It must be noted that, in the technique practiced in this field, we are seeking to follow a quick therapy which prescribes the application of the active product in contact with the body of the treated person or animal during the shortest time possible; thus, we consider as appropriate products that destroy after one application the totality of parasites.

Up to nowadays, extracts from Derris Elliptica, Tephrosia Vogelü and Louchocarpus Vicon, titrating about 40% of rotenone have been used for the treatment of pediculosis. The extract is an oleoresin very irritant for the skin and toxic for the bones; it is fragile, since the active principle, rotenone, is destroyed by light and difficult to use being hardly soluble in solvents compatible with a skin application.

In spite of this, the present invention allows us to produce, from rotenone, a composition which is perfectly convenient to skin applications, without any risk of irritation or intoxication. In fact, the invention achieves a composition which is not only harmless to human or animal skin, but also biodegradable and—consequently—does not leave any residue on the treated subjects. One particular, important example of this advantage resides in the treatment against sheep scab: the wool of the treated animals does not keep the rotenone from a composition according to the invention, whereas such an insecticide as "Lindane" is present even in the clothes made from the wool coming from sheep that have been treated against scab.

The invention results from the unexpected observation that the disadvantages of the rotenone based insecticide disappear, when this product does not contain any longer, or contains, at the most, a very diminished proportion of derivatives or such products which, normally accompany rotenone extract of plants.

Hence must we eliminate, or reduce to a minimum content, the various compounds, known by such names as sumatrol, biliptone, degueline toxicarol, malacol and the like, which we usually find with rotenone in natural extracts. In contrast, not only there a question of eliminating the dihydrorotenone $C_{23}H_{24}O_6$ bearing 2H more than rotenone $C_{23}H_{22}O_6$, but also—according to a particular feature of the invention—we would better use it in conjunction with rotenone, or alone, in the specific compositions of insecticides.

Admitting for rotenone the structure of tetrahydro-1, 2, 12, 12a dimethoxy-8,9 (méthyl-1-ethenyl)-2benzo [1]-pyrano furol (3,4,b) benzoyran (2, 3, h)[1] one 6 (6aH), that of the correspondant dihydrorotenone would be similar, but with an alcohol function in 6 (6aH) instead of ketone.

In order to ensure the advantages of the compositions according to the invention, the used rotenone or/and dihydrorotenone should not contain more than 10% by weight of cetonic derivatives, such as sumatrol, biliptone, degueline and the like, mentioned earlier. Preferably, the product according to the invention titrates at least 99% of pure rotenone or/and its dihydroderivative.

The insecticides according to the invention, being used in a solution of organic solvents, the latter have an important function: they should be harmless for the humans and animals other than insects, which eliminates chlorous solvents; they should dissolve the active products well enough to produce from them the necessary concentrations, generally about 0.05 to 10% by weight, and most often 0.1 to 5% in the composition to be applied as an insecticide.

Thanks to the publication of French Patent 2.448.856, we know various esters of phthalic, benzoic, benzylic, phosphorous, phosphoric and mellitic acids, which are convenient as solvents of rotenone and can—consequently—be used according to the present invention.

Another category of harmless solvents, which are convenient, comprises alkylene-glycols, particularly in $C_2$ to $C_{18}$. Hence can we use advantageously, for example, glycols of propylene, butylene, pentylene, hexylene, octylene, monylene, decylene etc. . .

In addition, there is at present a variety of useful solvents especially for cosmetic products, made up of linear and cyclic polyalkyl siloxanes; in particular such liquids with alkyls of in $C_1$ to $C_6$ are convenient for the preparation of insecticide compositions according to the invention. Such solvents as polydimethyl cyclosiloxanes and the hexamethyl disiloxane are readily available on the market.

It should be noted that derived dihydro, or reduced rotenone, is generally more soluble in different solvents than rotenone itself, so we can get more concentrated solutions, when a stronger insecticide action is needed.

According to an alternative of the invention, the rotenone composition is added to a small proportion of phenol, terpene, or to the two types of such compounds at the same time. This addition achieves a more efficient penetration of rotenone to the innermost hosts of insects and their eggs.

As phenols, we can use, for example, thymol, eugenol, iso-eugenol, galacol, resorcinol, hexyl-6 resorcinol and others.

Among the terpenes, convenient as additions to compositions according to the invention, we can name, as an example, myrcene, linalol, menthane, menthadiene (terpinene, terpinolene, limonene), pinene, camphane, camphene, bornylene, etc. . . . They can—of course—be taken under the form of their containing oils, such as turpentine, citronnella, lavender oils or the like.

The content of phenols or/and terpenes in the composition is not critical: it may vary, for instance, between about 0.05 and 5% by weight for each one of these adjuvants. It is, most often, of the same rate as that of rotenone or/and dihydrorotenone.

A special form of implementation of the invention consists in including in the composition spherules of small dimensions of a polymer capable of adsorbing, or of fixing through other bonding forces rotenone or/and reduced rotenone, from the above described solution.

Although the use of suspensions of micro or nanospheres of polymers, in cosmetic products is known, its application to insecticides formed by a rotenone or/and dihydrorotenone organic solution is unexpected. In fact, nothing could enable to foresee a priori that such an application would bring about an advantage: now, experience proved that in the presence of polymeric spherules in the rotenone composition, any hatching of a new generation of insects, some days after treatment, is avoided. So, unlike what happens with the known insecticides, the nits, remaining after the destruction of insects, cannot hatch. It is a surprising result, which makes of compositions according to the invention a remarkable means of parasite destruction on human or animal body; thus one can easily fight against sheep scab, pedicules, hypoderma bovis, hypoderma tincatum, the larva of cochlionyiac hominivorax, lucilia sericata, lucilia euprina etc. . . .

Microspheres of different polymers, and their technique of preparation are known. So they will not be described here. We can find the description, for example, in the patents FR 1.572.106 and 2.304.326, EP 0.064.967 or EP 0.274.961; but it is not an issue of achieving a complete insecticide effect (insects and their eggs) as in the present invention. Although the invention could relate to microscopic spherules of various sizes, preferably of dimensions not exceeding 1000 nm, the preferred sizes range between 50 and 500 nm or, even better, between 60 and 300 nm. The preferred size of the particles depends on the nature of the polymer that constitues them.

Particles, which are convenient to achieving the invention, can be chosen among the various known polymeric microspheres, full or empty, as long as they are insoluble in the medium liquid used. Anyway, the latter is, most often, chosen among rotenone solvents, referred to earlier; it can be such a liquid as, for example, a polyol such as glycol or glycerine, a polyol ether or ester, alcohol etc..

Thus, are convenient to the application according to the invention, scatterings of microparticles especially nanospheres, in polymers such as polysaccharides, polyamides, polyalkylenes, polyarylalkylenes, polyalkylidenes, polysilicones and others; in any of these classes, numerous derivatives and copolymers could be used. For example, we can use polysaccharides such as xanthane, scleroglucane, pectines, starch, cellulose, cyclodextrines, carboxymethylcellulose, hydroxy-cellulose, alkyl-cellulose, dextrine, polysiloxanes etc.

As far as the polyaryl-alkylenes are concerned, we can name polystyrene and especially its copolymers, particularly with ethylenic esters, especially acrylates or methacrylates of different alkyls, of hydroxy-alkyls, with methacryl- or acrylamide. Similarly, are convenient the vinylic resins, for example polyvinyl acetate. Besides, polysiloxanes have proved to be very useful.

Generally, products according to the invention have 0.1 to 10% by weight, and more often 0.3 to 3%, of the above defined spherules, the chosen content depending on the nature of the polymer(s), on the size of particles, on their affinity with the active substances and on the nature and proportion of the liquid of the scattering.

According to what preceeds, the composition according to the invention is composed, by weight, in principle, of: 0.05 to 10% of pure rotenone or/and reduced pure rotenone, of 0.1 to 10% of polymeric spherules, and of 80 to 99.4% of liquid or mixture of liquids having in their solution the rotenone compound and in suspension said spherules.

A practical operational mode for the preparation of such a composition comprises the following steps of : (A) dissolving the rotenone compound in its specific solvent, especially chosen among those mentioned earlier in the present description; (B) scattering the spherules in a non solvent; mixture of the solution (A) with the suspension (B) in addition, we should often add a solvent (C) in order to avoid the precipitation of the rotenone compound due to the addition of the non solvent (B).

Thus, as a non restrictive example, a particular preparation contains : the solution of 0.4 g of purified rotenone to (99.2%) in 15 g of lauryl; addition of 0.15 g of nanospheres of polysiloxane, from 60 to 300 nm, scattered in 23 g of ethanol ; dilution of the mixture with 61 g of hexamethyl disiloxane, a solvent that is known on the market under the tradename "DIMETHYLCONE", which guarantees the composition's homogeneity. The contents by weight are (%)

| | |
|---|---|
| pure rotenone | 0.40% |
| spherules of polysiloxane | 0.15% |
| lauryl benzoate | 15.00% |
| ethanol | 23.00% |
| hexamethyl disiloxane | 61.45% |
| | 100.00% |

Of course, in compositions containing ethanol or another alcohol, the proportion of the latter does not exceed the content that would cause the precipitation of rotenone.

Another operational mode consists in replacing the spherule suspension B by a powder of it, the preparation of spherules even extremely small in the pulverulent state being known as such.

It is also possible to produce the composition according to the invention by scattering, in rotenone solution A, a polymerizable monomer, and to have the composition undergo polymerization in the scattered state in this solution. This type of polymerization is described in the published patent FR-2.649.888 (Example 2).

The invention can be practised according to the above mentioned embodiments, whether the solvent of the rotenone agent and its possible additives be miscible or not with the liquid that holds the spherules in supension; in the absence of miscibility, it is convenient to add an appropriate tensioactive compound allowing a stable emulsion.

An alternative of the above mentioned processes includes an additional operation, in the end, namely the elimination of the remaining liquids. This can be achieved through a conventional operation, such as centrifugation, ultrafiltration, distillation—in vacuum if it is to happen-precipitation by a non solvent, etc.. Thus, the desired insecticide is obtained in the powder state, quite practical in certain cases and advantageous at least thanks to the fact that the choice of a liquid supported by the treated subject is avoided.

The product can also be present in the form of a cream or paste very convenient to certain applications; to obtain it, the liquid of the composition can be eliminated incompletely or thoroughly, the remaining being incorporated in a cream, foam or paste of therapeutic or/and cosmetic quality.

The invention is illustrated by the following non restrictive examples.

EXAMPLE 1

Treatment of pediculosis

Using hexylene glycol as a solvent, we prepared three rotenone solutions:

I—of 0.65% of commercial rotenone extract, of 45% of rotenone;

II—of 0.3% of purified rotenone, titrating 99.3% of this compound;

III—of 0.3% of purified rotenone (99.3%), reduced in the way described in the example 9.

On the other hand, we made up four sets of louse-infested subjects, all to the same degree of infestation, insofar as the number of lice is concerned as well as the vitality of nits. A first set of 10 untreated subjects, served as a model, the remaining three sets, as thirty subjects each, underwent treatments respectively with the three solutions I, II, III.

Table 1 of the results, below, relates the evolution during four days (D-0 to D-4); D-0 meaning "Day zero", is that of the subject' survey, the selection, the counting, then the first insecticide application.

On day D-1: there were the counting and the second application.

On day D-2: a counting and the third application.

On day D-3: only a counting.

On day D-4: counting of surviving lice.

The numbers of living insects, found, are shown in the vertical columns.

TABLE 1

| Composition | D-0 | D-1 | D-2 | D-3 | D-4 |
|---|---|---|---|---|---|
| I | 10 | 4 | 2 | 3 | 6 |
| II | 10 | 2 | 3 | 2 | 3 |
| III | 10 | 2 | 1 | 2 | 0 |

We find back the usual behaviour with the conventional composition I, 3 applications of which do not prevent the insects from reappearing on the fourth day. This phenomenon is considerably dimmed by pure rotenone, composition II, and seems to be eradicated by the third application (D-3) through the use of reduced rotenone (III). The use of pure rotenone and its reduction product, therefore, brings about a tremendous progress compared to that of the usual, commercial rotenone extract.

EXAMPLE 2

In the conditions described in example 1, we tried, comparatively with the compositions II and III suspensions of polysiloxane spherules of about 100 nm of average diameter:

| IV | and V |
|---|---|
| 0.29% pure rotenone | 0.29% reduced rotenone |
| 0.50% nanospheres | 0.50% nanospheres |
| 99.21% hexamethyleneglycol | 99.21% hexamethyleneglycol |

Table 2 gathers the results of these tests.

TABLE 2

| Composition | D-0 | D-1 | D-2 | D-3 | D-4 |
|---|---|---|---|---|---|
| II-pure rotenone | 10 | 3 | 2 | 2 | 4 |
| IV-pure rotenone. + nanospheres | 10 | 3 | 1 | 0 | 0 |
| III-pure rotenone,reduced | 10 | 1 | 3 | 1 | 0 |
| V-pure rotenone,reduced + nanospheres | 10 | 2 | 0 | 0 | 0 |

We can notice that, in the presence of polymeric spherules, the pure rotenone and its product of reduction (II and III) yield even more remarkable results than with only the solvent. Table 2 shows well that, starting from the second day, the destruction of insects is practically complete; besides, 0 on the fourth day means that the eggs could not hatch, which represents a notable advantage.

EXAMPLE 3

On each of the days D-0, D-1, D-2, D-3 and D-8, adult lice, of comparable age, having been in contact with treated hair by the compositions according to the invention, were shared in boxes. The same was done for lice taken from untreated, model hair. Death or survival of these insects was noticed 12 or 24 hours later.

Table 3 gives the number of living lice, at the beginning, after 12 and 24 hours.

TABLE 3

| | Beginning | 12 H. later | 24 H. later |
|---|---|---|---|
| | Composition III, being a solution of 0.29% of reduced rotenone. | | |
| D-0 | 40 | 32 | 4 |
| D-1 | 17 | 7 | 0 |
| D-2 | 16 | 13 | 1 |
| D-4 | 15 | 8 | 2 |
| D-8 | 13 | 11 | 0 |
| | Composition V (III + nanospheres) | | |
| D-0 | 14 | 4 | 0 |
| D-1 | 65 | 5 | 0 |
| D-2 | 16 | 8 | 0 |
| D-4 | 13 | 11 | 0 |
| D-8 | 15 | 12 | 0 |

It is striking to see that with the composition V, there is no surviver whatever the number of applications is; especially, since the line D-0 corresponds to the first application, as set out in example 1, it can be seen that this unique application is enough to kill all the lice within 24 hours, if they are affected by composition V. It is a valuable advantage, since with other insecticides, several applications are always necessary. So there is a persistence of the active principle.

EXAMPLE 4

Capillary lotion

| Purified rotenone of 99% | 0.35 g |
|---|---|
| Nanosphere of methyl polystyrene methacrylate (60/40) | 0.60 g |
| Lavender oil | 1.00 g |
| Hexylene glycol | 98.05 g |

EXAMPLE 5

Another capillary lotion

| | |
|---|---|
| Reduced rotenone to 99% | 0.3 g |
| Lavender oil | 1.0 g |
| Thymol | 0.5 g |
| Butylene glycol | 98.2 g |

EXAMPLES 6 to 8

Capillary lotions

| | 6 | 7 | 8 |
|---|---|---|---|
| Pure rotenone of 99.5% | 0.3 | — | 0.3 g |
| Pure reduced rotenone | — | 0.3 | — |
| Lavender oil | 0.5 | 0.5 | 0.5 |
| Thymol | 0.2 | 0.2 | 0.5 |
| Spherules 60–300 nm of polysiloxane | — | 0.6 | 0.5 |
| Lauryl benzoate | 40 | 25.4 | 40 |
| Poly-dimethyl cyclosiloxane | 59 | 74 | 58.5 |

EXAMPLE 9

Reduced rotenone preparation

From a natural extract of rotenone a 99.2% pure rotenone is first prepared; 10 g of this pure product, 0.025 mole of rotenone, are put in suspension in 50 ml of methanol, and the suspension is maintained at 0° C. Pastilles of sodium borohydride $NaBH_4$ are then slowly introduced in the suspension.

When hydrogen exhalation is over, the suspension is filtrated; 200 ml of diethylic ether are added to the separated solids, then 200 ml of water, stirring vigorously.

To the liquid environment are then added about 40 ml of HCl N, until pH is 6.5 to 7, then the solution is allowed to settle and a sample is taken from the ether phase. Then, the solution is washed three times successively, stirring, each time, with 250 ml of water, the solution is allowed to settle and separated from the ether phase. The latter is finally dried on sodium sulfate, filtrated and evaporated, which leaves 10 g of reduced, pure rotenone.

Note: The subjects of the experiments were children from 6 to 10 years old.

We claim:

1. An insecticide composition comprising:
   approximately 0.05% to 10% by weight of at least one active agent selected from the group consisting of rotenone, reduced rotenone and a mixture of rotenone and reduced rotenone, wherein said active agent is at least 90% pure;
   microscopic polymer spherules, wherein said active agent is adsorbed to the surface of said spherules and wherein said polymer is selected from the group consisting of polysaccharide, polyamide, polyalkylene, polyarylalkylene, polyalkylidene and polysiloxane; and
   approximately 80 to 95.5% of a carrier or diluent.

2. A composition according to claim 1, wherein said carrier or diluent comprises a solvent selected from the group consisting of ester of phthalic, benzoic, benzylic or mellitic acid, a $C_2$ to $C_8$ alkylene glycol and a linear or cyclic polyalkyl-siloxane.

3. A composition according to claim 2, wherein said solvent is selected from the group consisting of lauryl benzoate, ethanol and hexamethyl-disiloxane.

4. A composition according to claim 1 wherein said active agent is at least 99% pure.

5. A composition according to claim 1 wherein said spherules have dimensions of less than approximately 1000 nm.

6. A composition according to claim 1 wherein said spherules have dimensions of approximately 50–500 nm.

7. A composition according to claim 1 wherein said composition is in a form selected from the group consisting of a paste, a cream and a foam.

8. A method of destroying parasites on a human or animal body, comprising the step of:
   applying to a human or animal in need of such treatment a composition comprising:
   approximately 0.05% to 10% by weight of at least one active agent selected from the group consisting of rotenone, reduced rotenone and a mixture of rotenone and reduced rotenone, wherein said active agent is at least 90% pure;
   microscopic polymer spherules, wherein said active agent is adsorbed to the surface of said spherules and wherein said polymer is selected from the group consisting of polysaccharide, polyamide, polyalkylene, polyarylalkylene, polyalkylidene and polysiloxane; and
   a carrier, diluent or adjuvant.

9. A method according to claim 8 wherein said carrier or diluent comprises a solvent selected from the group consisting of ester of phthalic, benzoic, benzylic, or mellitic acid, a $C_2$ to $C_8$ alkylene-glycol and a linear or cyclic polyalkyl-siloxane.

10. A method according to claim 9 wherein said solvent is selected from the group consisting of lauryl benzoate, ethanol and hexamethyl-disiloxane.

11. A method according to claim 8 wherein said active agent is at least 99% pure.

12. A method according to claim 8 wherein approximately 0.1% to 3% by weight of said spherules are present.

13. A method of preparing a composition comprising the step of:
   dissolving approximately 0.05% to 10% by weight of at least one active agent selected from the group consisting of rotenone, reduced rotenone and a mixture of rotenone and reduced rotenone, wherein said active agent is at least 90% pure in a solvent to form a first solution; providing microscopic polymer spherules, wherein said polymer is selected from the group consisting of polysaccharide, polyamide, polyalkylene, polyarylalkylene, polyalkylidene and polysiloxane; and
   mixing said first solution and said spherules so that said active agent is adsorbed to the surface of said spherules.

14. A method according to claim 13 wherein said active agent and said spherules are mixed in the presence of a solvent selected from the group consisting of ester of phthalic, benzoic, benzylic, or mellitic acid, a $C_2$ to $C_8$ alkylene-glycol and a linear or cyclic polyalkyl-siloxane.

15. A method as recited in claim 13 wherein a surface active agent or a third solvent is mixed into said composition.

16. A method as recited in claim 14 further comprising the step of removing the liquid of the composition so that a powdered composition is produced.

17. A method as recited in claim 14 further comprising the step of mixing the composition with a compound selected from the group consisting of a cream, a paste and a foam.

18. A composition obtainable by a process comprising the steps of:

dissolving approximately 0.05% to 10% by weight of at least one active agent selected from the group consisting of rotenone, reduced rotenone and a mixture of rotenone and reduced rotenone, wherein said active agent is at least 90% pure in a solvent to form a first solution;

providing microscopic polymer spherules, wherein said polymer is selected from the group consisting of polysaccharide, polyamide, polyalkylene, polyarylalkylene, polyalkylidene and polysiloxane; and mixing said first solution and said spherules so that said active agent is adsorbed to the surface of said spherules.

19. A composition as recited in claim 18 wherein said process further comprises the step of removing the liquid of the composition so that a powdered composition is produced.

20. A method as recited in claim 8 wherein said adjuvant is selected from the group consisting of terpene, phenol and a mixture of terpene and phenol.

* * * * *